United States Patent
Porter

(10) Patent No.: US 7,249,469 B2
(45) Date of Patent: Jul. 31, 2007

(54) METHOD FOR SEPARATING A MULTICOMPONENT STREAM

(75) Inventor: John Roger Porter, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 384 days.

(21) Appl. No.: 10/991,778

(22) Filed: Nov. 18, 2004

(65) Prior Publication Data

US 2006/0101852 A1    May 18, 2006

(51) Int. Cl.
*F25J 3/00* (2006.01)
*C07C 2/68* (2006.01)
*C07C 5/22* (2006.01)
*C07C 15/12* (2006.01)

(52) U.S. Cl. ............... 62/620; 62/631; 585/467; 585/475

(58) Field of Classification Search ......... 62/620, 62/630, 631; 585/467, 475
See application file for complete search history.

(56) References Cited

U.S. PATENT DOCUMENTS

| | | | |
|---|---|---|---|
| 2,471,134 A | 5/1949 | Wright | 196/100 |
| 3,367,846 A | 2/1968 | Uitti et al. | |
| 3,437,708 A | 4/1969 | Gantt | 260/671 |
| 3,812,197 A * | 5/1974 | Suggitt et al. | 585/475 |
| 3,862,254 A | 1/1975 | Eisenlohr et al. | |
| 4,011,276 A | 3/1977 | Chu | 260/672 T |
| 4,016,219 A | 4/1977 | Kaeding | 260/672 T |
| 4,041,091 A | 8/1977 | Henry | 260/672 T |
| 4,098,837 A | 7/1978 | Chu | 260/672 T |
| 4,137,195 A | 1/1979 | Chu | 252/437 |
| 4,160,788 A | 7/1979 | Young | 585/475 |
| 4,182,923 A | 1/1980 | Chu | 585/475 |
| 4,230,533 A * | 10/1980 | Giroux | 203/1 |
| 4,233,139 A | 11/1980 | Murrell et al. | 208/112 |
| 4,246,073 A | 1/1981 | Umeda et al. | 203/25 |
| 4,247,368 A | 1/1981 | Bannon et al. | 202/158 |
| 4,306,944 A | 12/1981 | Murthy et al. | 203/77 |
| 4,402,867 A | 9/1983 | Rodewald | 252/455 Z |

(Continued)

FOREIGN PATENT DOCUMENTS

DE          3514365       10/1985

(Continued)

OTHER PUBLICATIONS

Abstract for DE3514365, published Oct. 31, 1985, entitled "Distn. System Having Evaporator and Condenser—with Two Columns Interconnected from Different Levels" (see AX).

(Continued)

*Primary Examiner*—William C. Doerrler

(57) ABSTRACT

This invention relates to a method for separating a stream having benzene, toluene and alkyl benzene, said method comprising: feeding the stream into a first distillation column, wherein the stream comprises between about 60 mole percent to about 85 mole percent toluene, between about seven mole percent to about 20 mole percent benzene, and between about seven mole percent to about 20 mole percent alkyl benzene; separating the steam into a first mixture stream and a second mixture stream; feeding the first mixture stream and the second mixture stream into a distillation system; separating the first mixture stream and the second mixture stream into a first product stream, a system recycle stream, and a second product stream.

20 Claims, 4 Drawing Sheets

U.S. PATENT DOCUMENTS

| | | | |
|---|---|---|---|
| 4,430,102 A | 2/1984 | Tedder | 62/24 |
| 4,436,540 A | 3/1984 | Dowd et al. | 62/30 |
| 4,533,533 A | 8/1985 | Dewing et al. | 423/328 |
| 4,677,239 A | 6/1987 | Dewing et al. | 585/475 |
| 4,721,824 A | 1/1988 | McWilliams et al. | 585/448 |
| 4,994,152 A | 2/1991 | Kaibel et al. | 203/75 |
| 5,004,854 A * | 4/1991 | Yan | 585/489 |
| 5,230,217 A | 7/1993 | Agrawal et al. | 62/22 |
| 5,289,688 A | 3/1994 | Agrawal | 62/24 |
| 5,371,312 A | 12/1994 | Lago et al. | 585/475 |
| 5,448,005 A | 9/1995 | Eccli et al. | 585/812 |
| 5,498,814 A | 3/1996 | Chang et al. | 585/475 |
| 5,498,822 A | 3/1996 | Eccli et al. | 585/816 |
| 5,513,497 A | 5/1996 | Agrawal et al. | 62/651 |
| 5,552,357 A | 9/1996 | Lago et al. | 502/63 |
| 5,554,274 A | 9/1996 | Degnan et al. | 208/111 |
| 5,573,645 A | 11/1996 | Pickering, Jr. | |
| 5,607,888 A | 3/1997 | Chang et al. | 502/64 |
| 5,625,103 A | 4/1997 | Abichandani et al. | 585/475 |
| 5,634,356 A | 6/1997 | Agrawal et al. | 62/646 |
| 5,659,098 A | 8/1997 | Beck et al. | 585/475 |
| 5,678,426 A | 10/1997 | Agrawal et al. | 62/647 |
| 5,680,775 A | 10/1997 | Manley | 62/630 |
| 5,692,395 A | 12/1997 | Agrawal et al. | 62/630 |
| 5,866,740 A | 2/1999 | Mikitenko et al. | 585/470 |
| 5,902,460 A | 5/1999 | Gerhold | 203/99 |
| 5,953,936 A | 9/1999 | Agrawal et al. | 62/630 |
| 5,970,742 A | 10/1999 | Agrawal et al. | 62/630 |
| 5,990,365 A | 11/1999 | Chang et al. | 585/475 |
| 6,060,634 A * | 5/2000 | Mikitenko et al. | 585/814 |
| 6,106,674 A | 8/2000 | Agrawal et al. | 203/75 |
| 6,114,592 A | 9/2000 | Gajda et al. | 585/475 |
| 6,133,470 A | 10/2000 | Beck et al. | 560/77 |
| 6,147,272 A | 11/2000 | Mikitenko et al. | 585/812 |
| 6,160,191 A | 12/2000 | Smith et al. | 585/475 |
| 6,173,584 B1 | 1/2001 | Agrawal | 62/620 |
| 6,191,331 B1 | 2/2001 | Boldingh | 585/475 |
| 6,250,106 B1 | 6/2001 | Agrawal | 62/643 |
| 6,263,700 B1 | 7/2001 | Agrawal et al. | 62/646 |
| 6,286,335 B1 | 9/2001 | Agrawal | 62/631 |
| 6,323,381 B1 * | 11/2001 | Nacamuli et al. | 585/475 |
| 6,347,533 B1 | 2/2002 | Tung | 62/620 |
| 6,359,185 B1 | 3/2002 | Boldingh et al. | 585/475 |
| 6,462,247 B1 | 10/2002 | Kelly et al. | 585/475 |
| 6,524,551 B2 | 2/2003 | Dhingra | 423/706 |
| 6,551,465 B1 | 4/2003 | Van Zile et al. | 202/158 |
| 6,558,515 B1 | 5/2003 | Steacy | 203/1 |
| 6,774,273 B2 | 8/2004 | Xie et al. | 585/304 |
| 7,109,389 B2 * | 9/2006 | Kong et al. | 585/302 |
| 2003/0116420 A1 | 6/2003 | Kaibel et al. | 203/1 |
| 2004/0011706 A1 | 1/2004 | Kaibel et al. | |

FOREIGN PATENT DOCUMENTS

| | | |
|---|---|---|
| DE | 4322725 | 12/1995 |
| JP | 9299702 | 11/1997 |
| JP | 10057703 | 3/1998 |
| JP | 10057704 | 3/1998 |
| RU | 1351966 | 11/1997 |
| RU | 2105589 | 2/1998 |

OTHER PUBLICATIONS

Abstract for RU2105589, published Feb. 27, 1998, entitled "Hydrocarbon Mixture Separation by Recitification . . . ", (see BB).

Abstract for SU1351966, published Nov. 15, 1997, entitled "Petroleum Fractions Separator—Derives Light Intermediate Fraction Contg . . . " (see BC).

* cited by examiner

METHOD FOR SEPARATING A MULTICOMPONENT STREAM

FIELD OF THE INVENTION

This invention relates generally to energy-efficient distillation systems for the separation of a multicomponent fluid feed. More particularly, this invention relates to separation systems for the separation of fluid mixtures having benzene, toluene, and alkyl benzene.

BACKGROUND OF THE INVENTION

A significant problem in the chemical and petroleum industry is the high energy costs associated with the separation of mixtures by distillation, and in particular with the separation of fluid streams having three or more components. This has become especially true in recent years with the substantial rise in energy costs. As a result, there is a need to develop distillation systems that provide for adequate separation of the components, at a lower energy cost. Some fully thermally coupled distillation systems provide some energy cost savings; however, due to control difficulties these distillation systems have generally not been commercially used. Thus there is a need for energy efficient methods to separate fluid streams. The present invention answers this need by providing a method and apparatus, which separates a mixture of benzene, toluene, and alkyl benzene, wherein a relatively high portion of toluene is present in the feed, while reducing the overall heat duty required by the distillation systems.

A conventional method for the separation of benzene, toluene, and alkyl benzene is disclosed in U.S. Pat. No. 4,246,073 where the initial feed stream contains a molar ratio of benzene-toluene-alkyl benzene at about 3:2:1.

SUMMARY OF THE INVENTION

This invention relates to a method for separating a stream having benzene, toluene and alkyl benzene, said method comprising: feeding the stream into a first distillation column, wherein the stream comprises between about 60 mole percent to about 85 mole percent toluene, between about seven mole percent to about 20 mole percent benzene, and between about seven mole percent to about 20 mole percent alkyl benzene; separating the steam into a first mixture stream and a second mixture stream; feeding the first mixture stream and the second mixture stream into a distillation system; separating the first mixture stream and the second mixture stream into a first product stream, a system recycle stream, and a second product stream.

This invention relates to a method for separating a stream having benzene, toluene and alkyl benzene, said method comprising: feeding the stream into a first distillation column, wherein the stream comprises between about 60 mole percent to about 85 mole percent toluene, between about seven mole percent to about 20 mole percent benzene, and between about seven mole percent to about 20 mole percent alkyl benzene; separating the steam into a first mixture stream and a second mixture stream; feeding the first mixture stream and the second mixture stream into a distillation system; wherein said distillation system includes a second distillation column and a third distillation column, and wherein the method further comprises: feeding the first mixture stream into the second distillation column, separating the first mixture stream into a first product stream and a second recycle stream, feeding the second mixture stream into the third distillation column, separating the second mixture stream into a second product stream and a third recycle stream, wherein the system recycle stream comprises the second recycle stream and the third recycle stream.

This invention relates to a method for separating a stream having benzene, toluene and alkyl benzene, said method comprising: feeding the stream into a first distillation column, wherein the stream comprises between about 60 mole percent to about 85 mole percent toluene, between about seven mole percent to about 20 mole percent benzene, and between about seven mole percent to about 20 mole percent alkyl benzene; separating the stream into a first mixture stream and a second mixture stream; feeding the first mixture stream and the second mixture stream into a distillation system; wherein said distillation system includes a second distillation column and a third distillation column, and wherein the method is further comprising: feeding the first mixture stream into the second distillation column, separating the first mixture stream into a first product stream and a second recycle stream, feeding the second mixture stream into the third distillation column, separating the second mixture stream into a second product stream and a third recycle stream, wherein the system recycle stream comprises the second recycle stream and the third recycle stream, wherein at least a portion of the system recycle stream is fed into a toluene disproportionation unit; and having a fourth distillation column and a fifth distillation column, wherein a column feed stream is fed into the fourth distillation column, wherein the column feed stream comprises between about 10 mole percent to about 50 mole percent toluene, between about 20 mole percent to about 60 mole percent benzene, between about 0 mole percent to about 40 mole percent alkyl benzene, and between about 0 mole percent to about 10 mole percent impurities, the column feed stream is separated into a third product stream, a third mixture stream, and a fourth mixture stream, the third mixture stream is fed into the second distillation column, the fourth mixture stream is fed into the fifth distillation column, the fourth mixture stream is separated into a fourth recycle stream and a fourth product stream, and at least a portion of the fourth recycle stream is fed into the toluene disproportionation unit.

This invention relates to a method for separating a stream having benzene, toluene and alkyl benzene, said method comprising: feeding the stream into a divided wall column, wherein the stream comprises between about 60 mole percent to about 85 mole percent toluene, between about seven mole percent to about 20 mole percent benzene, and between about seven mole percent to about 20 mole percent alkyl benzene, and separating the stream into a first product stream, a system recycle stream, and a second product stream.

This invention relates to an apparatus comprising a toluene disproportionation unit, a first distillation column and a distillation system, wherein a stream having between about 60 mole percent to about 85 mole percent toluene, between about seven mole percent to about 20 mole percent benzene, and between about seven mole percent to about 20 mole percent alkyl benzene is fed into the first distillation column, and wherein a first mixture stream is fed from the first distillation column into the distillation system, and a second mixture stream is fed from the first distillation column into the distillation system, and at least a portion of a system recycle stream is fed from the distillation system into the toluene disproportionation unit.

This invention relates to a method for improving the operation of a distillation system, said distillation system having a toluene disproportionation unit fluidically connected to a first distillation column, wherein said first distillation column comprises a first overhead product pipe and a bottoms mixture pipe, wherein said bottoms mixture pipe is fluidically connected to a second distillation column, wherein said second distillation column comprises a second overhead product pipe and a first bottoms product pipe, said method including the steps of: reducing the heat duty on the first distillation column; fluidically connecting the first overhead product pipe to the second distillation column; increasing the heat duty on the second distillation column; and providing a first middle product pipe fluidically connected to the second distillation column; wherein the heat duty on the first distillation column and the heat duty on the second distillation column are changed in a manner that reduces the total heat duty by at least about 15 percent.

This invention relates to a method for separating a stream having benzene, toluene and alkyl benzene, said method comprising: feeding the stream into a first distillation column, wherein the stream comprises between about 60 mole percent to about 85 mole percent toluene, between about seven mole percent to about 20 mole percent benzene, and between about seven mole percent to about 20 mole percent alkyl benzene; separating the steam into a first mixture stream and a second mixture stream; feeding the first mixture stream and the second mixture stream into a distillation system; separating the first mixture stream and the second mixture stream into a first product stream, a system recycle stream, and a second product stream; and feeding at least a portion of the system recycle stream into a toluene disproportionation unit.

BRIEF DESCRIPTION OF THE FIGURES

A more complete appreciation of the claimed invention and many of the attendant advantages thereof will be readily obtained as the invention becomes better understood by reference to the following detailed description when considered in connection with the accompanying drawings, wherein:

Figure 1:
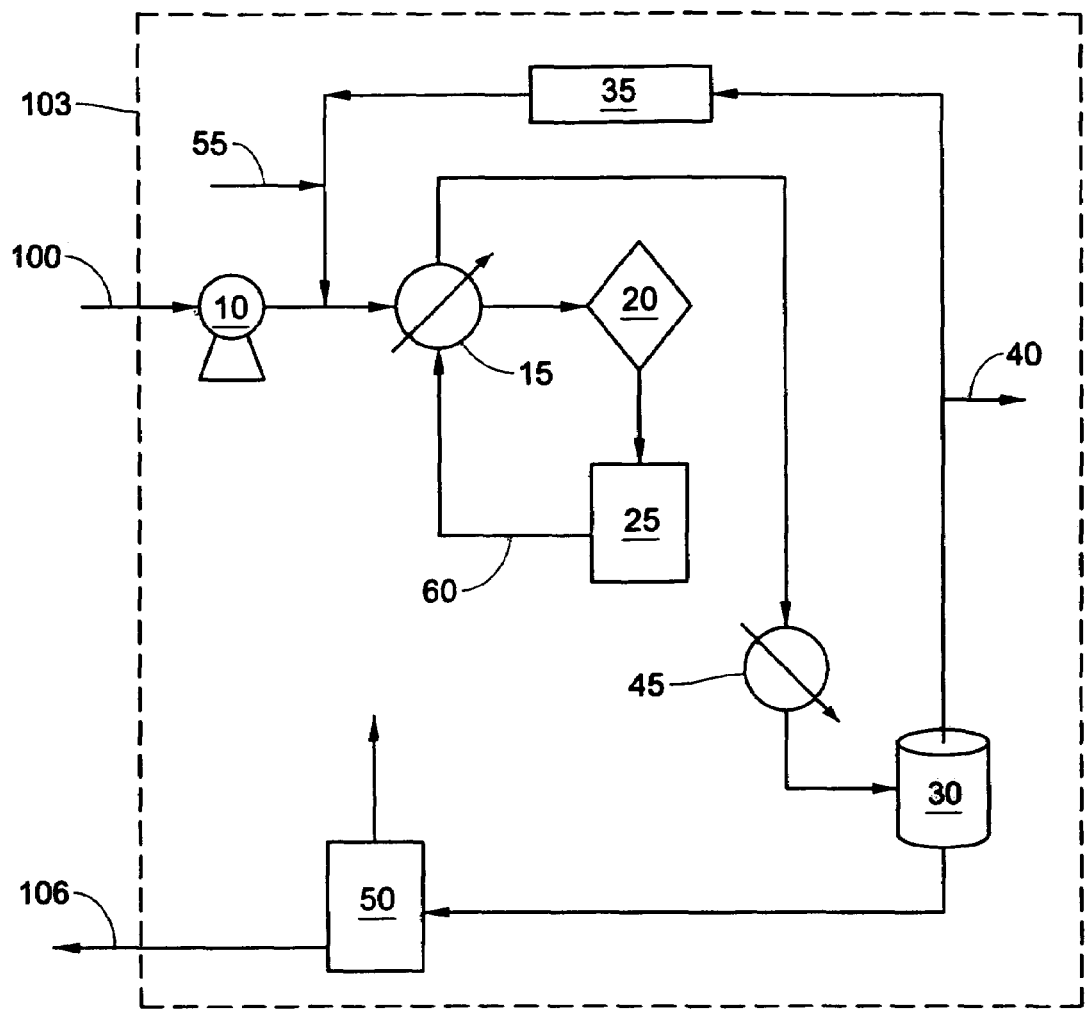
FIG. 1 is a schematic diagram of an embodiment of a toluene disproportionation unit 103.

As is apparent from the foregoing general description and preferred embodiments, while forms of the invention have been illustrated and described, various modifications can be made without departing from the spirit and scope of the invention. Accordingly, it is not intended that the invention be limited to the specific embodiments described herein.

DETAILED DESCRIPTION

This invention provides an energy efficient distillation system. In particular, the present invention is an enhanced distillation system for the separation of multicomponent mixtures comprising benzene, toluene, and alkyl benzene. For the purposes of this invention and the claims thereto the term alkyl benzene is defined to include the chemicals selected from the group consisting of all isomers of xylene as well as ethylbenzene and mixtures thereof i.e., alkyl benzene can only be p-xylene, o-xylene, m-xylene, ethylbenzene and mixtures thereof.

The mole percents recited herein are based on the total components within a given stream including impurities. The term 'theoretical stage' recited herein is meant to disclose both actual trays and packed beds. The theoretical stages are numbered from the top to the bottom. The total number of theoretical stages includes one stage for the reboiler and one stage for the condenser. Moreover, the total number of actual trays and/or the height of the packed bed can be calculated from the given theoretical stages by any of the chemical engineering conventions disclosed in *Distillation Design* by Kister, published by McGraw Hall 1992, which is incorporated by reference in full. The dashed lines of FIGS. 1-7 indicate optional equipment and optional streams, as explained below, with the following three exceptions: 1) the dashed line in FIG. 1 numbered 103, which indicates that the equipment and streams within the box represents the toluene disproportionation unit 103, 2) the dashed line in FIG. 3 numbered 130, which indicates that the equipment and streams within the box represents the distillation system 130, and 3) the dashed line in FIG. 4 numbered 170, which indicates that the equipment and streams within the box represents the equipment and streams of the actual plant, as explained below in Example 3 Plant.

With reference to FIG. 1, in an embodiment a reactor feed stream 100 is fed into a toluene disproportionation unit 103. The reactor feed stream 100 is disproportionated in the toluene disproportionation unit 103. The term toluene disproportionation unit includes all equipment necessary to disproportionate a toluene feed stream and prepare the stream for distillation. Such equipment, as shown in FIG. 1 for example, may include a pump 10, heat exchangers 15 and 45, a furnace 20, a toluene disproportionation reactor 25, a drum 30, a compressor 35, a purge valve 40, a distillation column 50, as well as other equipment which would be known to one of ordinary skill in the art. Continuing with reference to FIG. 1, the pressure of reactor feed stream 100 is increased by the pump 10 to a pressure necessary to run the toluene disproportionation reactor 25. In an embodiment the pump 10 increases the pressure of reactor feed stream 100 to between about from 1,000 to about 5,000 kPa, preferably from about 2,000 to about 3,500 kPa. In an embodiment, a hydrogen feed stream 55 feeds hydrogen into the reactor feed stream 100 at a location before the reactor feed stream 100 enters the toluene disproportionation reactor 25. Additionally, in an embodiment, the temperature of the reactor feed stream 100 is increased in a heat exchanger 15 and a furnace 20 to a temperature necessary to run the toluene disproportionation reactor 25 before the reactor feed stream 100 enters the toluene disproportionation reactor 25. In an embodiment the heat exchanger 15 and the furnace 20 increases the temperature of the reactor feed stream 100 to a temperature of from about 300° C. to about 500° C. In one embodiment, the effluent of the toluene disproportionation reactor 25 is an effluent stream 60. In this embodiment, the effluent stream 60 is cooled in heat exchangers 15 and 45 to about ambient temperature. Continuing with this embodiment, the drum 30 separates the effluent stream 60 into its vapor and liquid components. The vapor component of the effluent stream 60 is mostly hydrogen, which is then compressed in the compressor 35 and recycled into the hydrogen feed stream 55. The distillation column 50 operates to separate the light gases, such as $C_2$-$C_4$, and hydrogen from the heavier components within the effluent stream 60. Suitable toluene disproportionation reactors are those which disproportionate from about 10 mole percent to about 35 mole percent of the toluene feed into benzene and alkyl benzene, preferably from about 15 mole percent to about 30 mole percent of the toluene feed is disproportionated into benzene and alkyl benzene, more preferably from about 20 mole percent to about 30 mole percent of the toluene feed is disproportionated into benzene and alkyl benzene. U.S. Pat. No. 5,371,312 to Lago et al., U.S. Pat. No. 5,367,094 to Chung, and U.S. Pat. No. 5,365,004 to Beck et al., all of which are incorporated by reference in full, detail examples of suitable toluene disproportionation reactors.

In a preferred embodiment, the reactor feed stream 100 includes toluene, benzene, and alkyl benzene. Impurities may also be present in the reactor feed stream 100. Impurities may be water, and/or $C_1$-$C_{20}$ hydrocarbons, and/or such other materials that are entrained in the stream, excluding benzene, toluene, and alkyl benzene. In an embodiment the reactor feed stream 100 comprises about 85 mole percent to about 100 mole percent toluene, more preferably between about 95 mole percent to about 100 mole percent, most preferably between about 98 mole percent to about 100 mole percent. In an embodiment, the reactor feed stream 100 comprises between about 0 mole percent to about six mole percent benzene, more preferably between about 0 mole percent to about three mole percent benzene more preferably between about 0 mole percent to about two mole percent, more preferably between about 0 mole percent to about 5000 mole ppm, more preferably between about 0 mole percent to about 1000 mole ppm. In an embodiment, the reactor feed stream 100 comprises between about 0 mole percent to about six mole percent alkyl benzene, more preferably between about 0 mole percent to about three mole percent alkyl benzene, more preferably between about 0 mole percent to about two mole percent, more preferably between about 0 mole percent to about 5000. In another embodiment, the reactor feed stream 100 comprises between about 0 mole percent to about eight mole percent impurities, preferably between about 0 mole percent to about four mole percent, more preferably between about 0 mole percent to about one mole percent.

In an embodiment the stream 106 can be any stream, which contains toluene, benzene, alkyl benzene, and may have byproducts, wherein the stream 106 contains between about 60 mole percent to about 85 mole percent toluene, more preferably between about 65 mole percent to about 80 mole percent, most preferably between about 70 mole percent to about 75 mole percent; between about seven mole percent to about 20 mole percent benzene, more preferably between about 10 mole percent to about 16 mole percent benzene; between about seven mole percent to about 20 mole percent alkyl benzene, more preferably between about 10 mole percent to about 15 mole percent alkyl benzene; and between about 0 mole percent to about eight mole percent byproducts, preferably between about 0 mole percent to about three mole percent byproducts, more preferably between about 0 mole percent to about one mole percent byproducts. In one embodiment the stream 106 is the stream resulting from feeding the reactor feed stream 100 into the toluene disproportionation unit 103 i.e., the stream 106 is the result of cooling and distilling the effluent stream 60. In another embodiment, not shown in FIG. 1, the stream 106 is not the stream resulting from feeding the reactor feed stream 100 into the toluene disproportionation unit 103.

In one embodiment, the stream 106 contains between about 60 mole percent to about 85 mole percent toluene, more preferably between about 65 mole percent to about 80 mole percent, most preferably between about 70 mole percent to about 75 mole percent. In an embodiment, the stream 106 contains between about seven mole percent to about 20 mole percent benzene, more preferably between about 10 mole percent to about 16 mole percent benzene. In an embodiment, the stream 106 contains between about seven mole percent to about 20 mole percent alkyl benzene, more preferably between about 10 mole percent to about 15 mole percent alkyl benzene. In another embodiment, the stream 106 contains between about 0 mole percent to about eight mole percent byproducts, preferably between about 0 mole percent to about three mole percent byproducts, more preferably between about 0 mole percent to about one mole percent byproducts.

Figure 2:
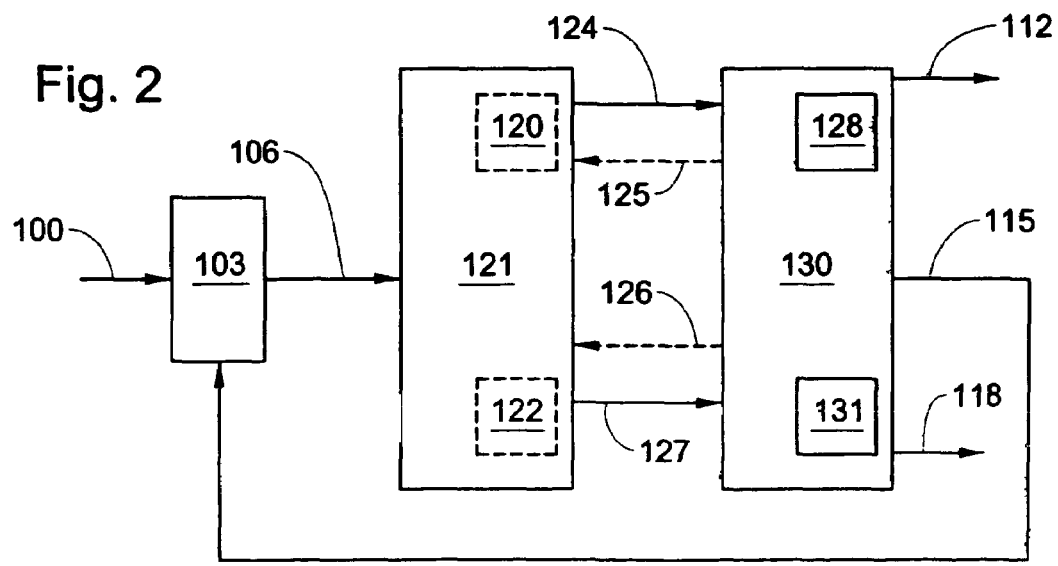
FIG. 2 is a schematic diagram of an embodiment showing a toluene disproportionation unit 103, a first distillation column 121, and a distillation system 130.

With reference to FIG. 2, the reactor feed stream 100, the toluene disproportionation unit 103, and the stream 106 were described in detail with reference to FIG. 1. Continuing with reference to FIG. 2, in an embodiment the stream 106 is fed into a first distillation column 121. The first distillation column 121 separates the stream 106 into a first mixture stream 124 and a second mixture stream 127. The first distillation column 121 can have a reboiler 122 and a condenser 120. The first mixture stream 124 and the second mixture stream 127 are fed into a distillation system 130. The distillation system separates the first mixture stream 124 and the second mixture stream 127 into a first product stream 112, a system recycle stream 115, and a second product stream 118.

Continuing with reference to FIG. 2, in an embodiment the first distillation column 121 has between about 30 theoretical stages and about 60 theoretical stages, preferably between about 35 theoretical stages and about 40 theoretical stages. In an embodiment the distillation system 130 is a distillation column having between about 50 theoretical stages and about 75 theoretical stages, preferably between about 60 theoretical stages and about 80 theoretical stages. In the embodiment where the distillation system 130 is a distillation column, the distillation system 130 has a second reboiler 131 and a second condenser 128. In an embodiment the stream 106 is fed into the first distillation column 121 at a location between about theoretical stage number 10 and about theoretical stage number 30, preferably between about theoretical stage number 15 and about theoretical stage number 20. The first distillation column 121 separates the stream 106 into a first mixture stream 124 and a second mixture stream 127. In an embodiment, the first mixture stream 124 is removed from the first distillation column 121 at a location between the top theoretical stage and the theoretical stage that is fifth from the top theoretical stage.

In an embodiment, the second mixture stream 127 is removed from the first distillation column 121 at a location between the bottom theoretical stage and the theoretical stage that is fifth from the bottom theoretical stage. The first mixture stream 124 and the second mixture stream 127 are fed into the distillation system 130. In an embodiment the first mixture stream 124 is fed into the distillation system 130 at a location between about theoretical stage number 40 and theoretical stage number 65, preferably between about theoretical stage number 45 and theoretical stage number 55. In an embodiment the second mixture stream 127 is fed into the distillation system 130 at a location between about theoretical stage number five and theoretical stage number 30, preferably between about theoretical stage number 10 and theoretical stage number 20.

The distillation system 130 separates the first mixture stream 124 and the second mixture stream 127 into the first product stream 112, the system recycle stream 115, and the second product stream 118. In an embodiment the first product stream 112 is removed from a location between the top theoretical stage of the distillation system 130 and the theoretical stage that is fifth from the top of the distillation system 130. In an embodiment the system recycle stream 115 is removed from a location between theoretical stage number 30 of the distillation system 130 and theoretical stage number 20 of the distillation system, 130. In an embodiment the second product stream 118 is removed from a location between the bottom theoretical stage of the distillation system 130 and the theoretical stage that is fifth from the bottom of the distillation system 130. In an embodiment the first distillation column 121 is thermally coupled with the distillation system 130. When the first distillation column 121 is thermally coupled to the distillation system 130 a vapor side stream 126 of the distillation system 130 is fed into the first distillation column 121 at the same stage as the second mixture stream 127 is withdrawn. Additionally, when the first distillation column 121 is thermally coupled to the distillation system 130 a liquid side stream 125 of the distillation system 130 is fed into the first distillation column 121 at the same stage as the first mixture stream 124 is withdrawn. When this configuration is implemented the reboiler 122 and condenser 120 are not necessary on the first distillation column. In an alternative embodiment, when the first distillation column 121 is thermally coupled to the distillation system 130 a vapor side stream 126 of the distillation system 130 is fed into the first distillation column 121 within plus or minus fives stages from the stage that the second mixture stream 127 is withdrawn. Additionally, in an alternative embodiment, when the first distillation column 121 is thermally coupled to the distillation system 130 a liquid side stream 125 of the distillation system 130 is fed into the first distillation column 121 within plus or minus five stages from the stage that the first mixture stream 124 is withdrawn.

In one embodiment the first product stream 112 contains between about 80 mole percent benzene to about 100 mole percent benzene, preferably between about 90 mole percent benzene to about 100 mole percent benzene. In another embodiment the first product stream 112 contains between about 0 mole percent to about five mole percent toluene, preferably between about 0 mole percent to about three mole percent toluene, and most preferably between about 0 mole percent to about 2.5 mole percent toluene. In yet another embodiment the first product stream 112 contains between about 0 mole percent impurities to about five mole percent impurities, preferably between about 0 mole percent impurities to about two mole percent impurities. In yet another embodiment the first product stream 112 contains between about 0 mole percent alkyl benzene to about two mole percent alkyl benzene, preferably between about 0 mole percent alkyl benzene to about one mole percent alkyl benzene.

In one embodiment the second product stream 118 contains between about 90 mole percent alkyl benzene to about 100 mole percent alkyl benzene, preferably between about 95 mole percent alkyl benzene to about 100 mole percent alkyl benzene, and most preferably between about 98 mole percent alkyl benzene to about 100 mole percent alkyl benzene. In another embodiment the second product stream 118 contains between about 0 mole to about five mole toluene, preferably between about 0 mole to about four mole toluene, and most preferably between about 0 mole to about three mole toluene. In yet another embodiment the second product stream 118 contains between about 0 mole percent impurities to about 10 mole percent impurities, preferably between about 0 mole percent impurities to about one mole percent impurities. In yet another embodiment the second product stream 118 contains between about 0 mole percent benzene to about two mole percent benzene, preferably between about 0 mole percent benzene to about one mole percent benzene.

In another embodiment the system recycle stream 115 contains between about 90 mole percent toluene to about 100 mole percent toluene, preferably between about 95 mole percent toluene to about 100 mole percent toluene, more preferably between about 98 mole percent toluene to about 100 mole percent toluene. In another embodiment the system recycle stream 115 contains between about 0 mole ppm benzene to about 20000 mole ppm benzene, preferably between about 0 mole ppm benzene to about 2500 mole ppm benzene, more preferably between about 0 mole ppm benzene to about 1500 mole ppm benzene. In yet another embodiment the system recycle stream 115 contains between about 0 mole ppm alkyl benzene to about 20000 mole ppm alkyl benzene, preferably between about 0 mole ppm alkyl benzene to about 5000 mole ppm alkyl benzene, more preferably between about 0 mole ppm alkyl benzene to about 3000 mole ppm alkyl benzene. In a preferred embodiment the system recycle stream 115 is fed back into the toluene disproportionation unit 103. In an alternative embodiment, only a portion of the system recycle stream 115 is fed back into the toluene disproportionation unit 103. In yet another embodiment none of the system recycle stream 115 is fed back into the toluene disproportionation unit 103.

In an embodiment, the first mixture stream 124 contains between about 40 mole percent to about 70 mole percent toluene, more preferably between about 55 mole percent to about 70 mole percent toluene, most preferably between about 55 mole percent to about 65 mole percent toluene. In an embodiment, the first mixture stream 124 contains between about 30 mole percent to about 60 mole percent benzene, preferably between about 35 mole percent to about 45 mole percent benzene. In yet another embodiment, the first mixture stream 124 contains between about 0 mole ppm alkyl benzene and about 20,000 mole ppm alkyl benzene, preferably between about 0 mole ppm alkyl benzene and about 1000 mole ppm alkyl benzene, more preferably between about 0 mole ppm alkyl benzene to about 500 mole ppm alkyl benzene. In yet another embodiment, the first mixture stream 124 contains between about 0 mole percent impurities to about 10 mole percent impurities, preferably between about 0 mole percent impurities to about five mole percent impurities, and most preferably between about 0 mole percent impurities to about two mole percent impurities. In an embodiment the first mixture stream 124 is a liquid at its bubble point. In an alternative embodiment the first mixture stream 124 is a subcooled liquid. In a preferred embodiment the first mixture stream 124 is a vapor at its dew point.

In an embodiment, the second mixture stream 127 contains between about 60 mole percent to about 85 mole percent toluene, more preferably between about 65 mole percent to about 80 mole percent toluene, most preferably between about 75 mole percent to about 80 mole percent toluene. In an embodiment, the second mixture stream 127 contains between about 14 mole percent to about 40 mole percent alkyl benzene, preferably between about 20 mole percent to about 30 mole percent alkyl benzene. In yet another embodiment, the second mixture stream 127 contains between about 0 mole ppm benzene and about 20,000 mole ppm benzene, preferably between about 0 mole ppm benzene and about 1000 mole ppm benzene, more preferably between about 0 mole ppm benzene to about 500 mole ppm benzene. In yet another embodiment, the second mixture stream 127 contains between about 0 mole percent impurities to about 10 mole percent impurities, preferably between about 0 mole percent impurities to about five mole percent impurities and most preferably between about 0 mole percent impurities to about two mole percent impurities.

In one embodiment, the total heat duty on the heating apparatus of the first distillation column 121 and the distillation system 130 is less than about 80,000 kJ/(kg mol product), preferably less than about 75,000 kJ/(kg mol product), more preferably about 70,000 kJ/(kg mol product), more preferably less than about 66,000 kJ/(kg mol product). Total heat duty is the amount of heat that is used in a distillation system in order to undergo distillation. In an embodiment the heat duty on the first distillation column 121 is less than 35,000 kJ/(kg mol product), preferably less than 30,000 kJ/(kg mol product), preferably less than 28,000 kJ/(kg mol product). In an embodiment the heat duty on the distillation system 130 is less than 45,000 kJ/(kg mol product), preferably less than 40,000 kJ/(kg mol product), preferably less than 38,000 kJ/(kg mol product). It is desirable to reduce cost by using the smallest amount of total heat duty necessary to distill the components. In one embodiment the heating apparatus is a reboiler. In one embodiment the heating apparatus of the first distillation column 121 is the reboiler 122 and the heating apparatus of the distillation system 130 is a second reboiler 131. In this embodiment the total heat duty is the sum of the heat duty on the reboiler 122 and the heat duty on the second reboiler 131. The units kJ/(kg mol product) mean 1000 Joules per 1000 grams of moles product from the toluene disproportionation unit.

Figure 3:
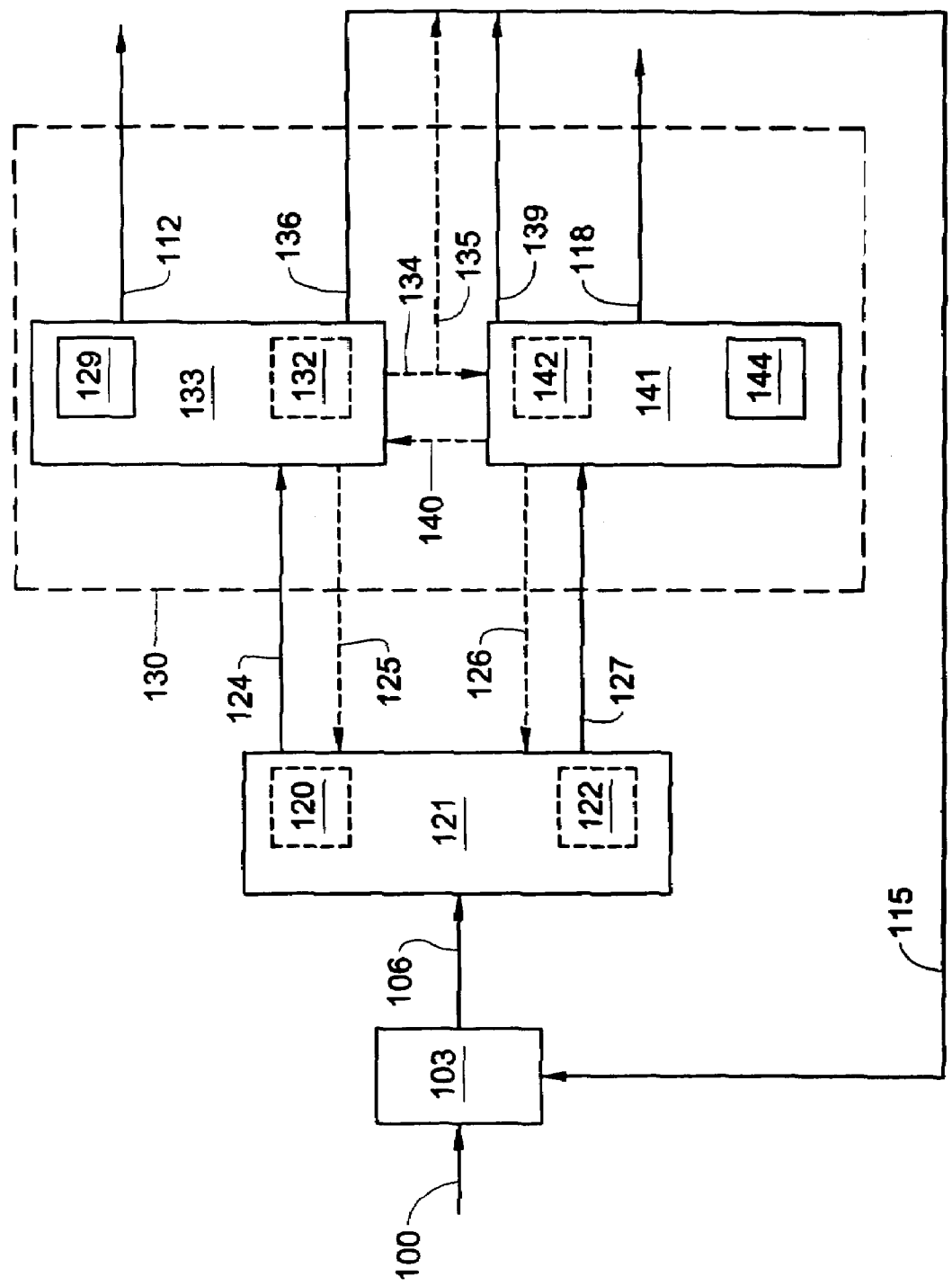
FIG. 3 is a schematic diagram of an embodiment showing a toluene disproportionation unit 103, the first distillation column 121, a second distillation column 133, and a third distillation column 141.

With reference to FIG. 3, a second distillation column 133 and a third distillation column 141 comprise the distillation system 130. The second distillation column 133 has a third condenser and an optional third reboiler. The third distillation column 141 has an optional fourth condenser and a fourth reboiler. In one embodiment the second distillation column 133 is thermally coupled to the third distillation column 141 by providing a second vapor stream 140, which is directly fed from the third distillation column 141 into the second distillation column 133, a second liquid stream 134, which is directly fed from the third distillation column 141 into the second distillation column 133, and a fifth recycle stream 135, which is optionally fed from the second liquid stream 134 into either the system recycle stream 115 or the second recycle stream 136. In another embodiment the second distillation column 133 and the third distillation column 141 are thermally coupled by using the fourth condenser 142 on the third distillation column 141 to act as the third reboiler 132 on the second distillation column 133. FIGS. 1 and 2 show and describe the reactor feed stream 100, the toluene disproportionation unit 103, the stream 106, the condenser, the first distillation column 121, the reboiler 122, the system recycle stream 115, the first mixture stream 124, the liquid side stream 125, the vapor side stream 126, and the second mixture stream 127. The second distillation column 133 has between about 15 theoretical stages and about 60 theoretical stages, preferably between about 20 theoretical stages and about 40 theoretical stages. The third distillation column 141 has between about 20 theoretical stages and about 60 theoretical stages, preferably between about 30 theoretical stages and about 50 theoretical stages. In an embodiment the first mixture stream 124 is fed into the second distillation column 133 at a location between about theoretical stage number 10 and about theoretical stage number 40, preferably between about theoretical stage number 12 and about theoretical stage number 25. The second distillation column 133 separates the first mixture stream 124 into the first product stream 112 and a second recycle stream 136. The first product stream 112 is removed from the second distillation column 133 at a location between the top theoretical stage and the theoretical stage that is fifth from the top theoretical stage. The second recycle stream 136 is removed from the second distillation column 133 at a location between the bottom theoretical stage and the theoretical stage that is fifth from the bottom theoretical stage. In this embodiment the second mixture stream 127 is fed into third distillation column 141 at a location between about theoretical stage number 15 and about theoretical stage number 35, preferably between about theoretical stage number 20 and about theoretical stage number 30. The third distillation column 141 separates the second mixture stream 127 into the second product stream 118 and a third recycle stream 139. The second product stream 118 is removed from the second distillation column 133 at a location between the bottom theoretical stage and the theoretical stage that is fifth from the bottom theoretical stage. The third recycle stream 139 is removed from the third distillation column 141 at a location between the top theoretical stage and the theoretical stage that is fifth from the top theoretical stage. The ranges of concentrations of the species found in the first mixture stream 124 the second mixture stream 127 the first product stream 112 and the second product 118 are defined above. In an embodiment, the ranges of concentrations of the species found in the second recycle stream 136 and the ranges of concentration of the species found in the third recycle stream 139 are the same as the ranges of concentrations of the species found in the system recycle stream 115. In a preferred embodiment the second recycle stream 136 and/or the third recycle stream 139 are, independently, fed back into the toluene disproportionation unit 103. In an alternative embodiment only a portion of the second recycle stream 136 and/or only a portion of the third recycle stream 139 are, independently, fed back into the toluene disproportionation unit 103. In yet another embodiment none of the second recycle stream 136 and/or none of the third recycle stream 139 are, independently, fed back into the toluene disproportionation unit 103. In an embodiment the system recycle stream 115 comprises the second recycle stream 136 and the third recycle stream 139.

In one embodiment, the total heat duty on the heating apparatuses of the first distillation column 121 the second distillation column 133 and the third distillation column 141 is less than about 80,000 kJ/(kg mol product), preferably less than about 75,000 kJ/(kg mol product), more preferably about 70,000 kJ/(kg mol product), more preferably less than about 66,000 kJ/(kg mol product). In an embodiment the heat duty on the first distillation column 121 is less than 35,000 kJ/(kg mol product), preferably less than 30,000 kJ/(kg mol product), preferably less than 28,000 kJ/(kg mol product). In an embodiment the heat duty of the second distillation column 133 in addition to the heat duty of the third distillation column 141 is less than 45,000 kJ/(kg mol product), preferably less than 40,000 kJ/(kg mol product), preferably less than 38,000 kJ/(kg mol product). In one embodiment the heating apparatus of the first distillation column 121 is the reboiler 122, the heating apparatus of the second distillation column 133 is the third reboiler 132, and the heating apparatus of the third distillation column 142 is the fourth reboiler 144.

Figure 4:
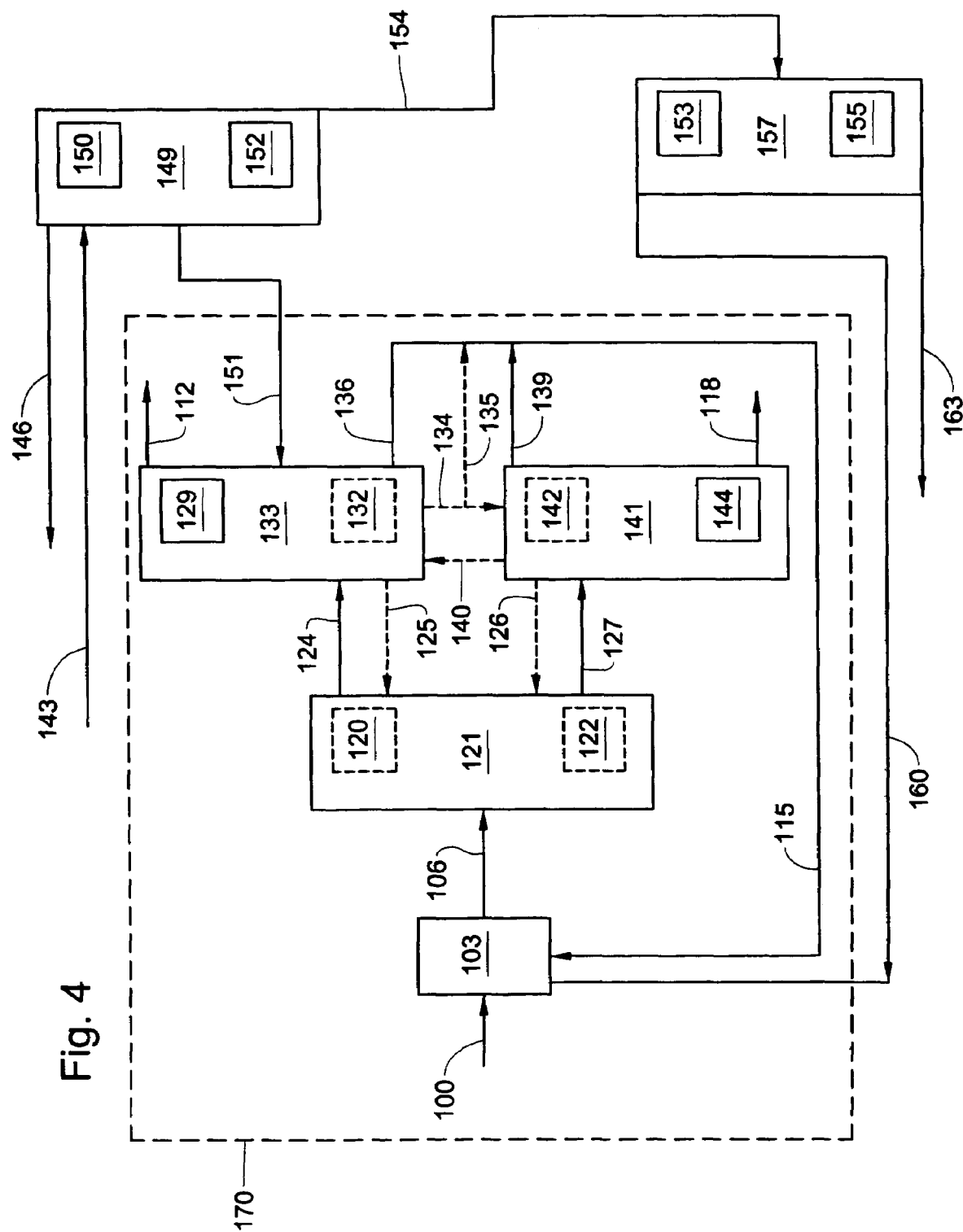
FIG. 4 is a schematic diagram of an embodiment showing a toluene disproportionation unit 103, a first distillation column 121, a second distillation column 133, a third distillation column 141, a fourth distillation column 149, and a fifth distillation column 157.

Referring to FIG. 4, in an embodiment the separation system of FIG. 3, as described above, further includes at least two additional distillation columns i.e., a fourth distillation column 149 and a fifth distillation column 157. The fourth distillation column 149 has a fifth condenser 150 and a fifth reboiler 152. The fifth distillation column 157 has a sixth condenser 153 and a sixth reboiler 155. FIGS. 1, 2, and 3 show and describe the reactor feed stream 100, the toluene disproportionation unit 103, the feed stream 106, the condenser 120, the first distillation column 121, the reboiler 122, the first mixture stream 124, the liquid side stream 125, the vapor side stream 126, the second mixture stream 127, the third condenser 129, the third reboiler 132, the second distillation column 133, the second liquid stream 134, the fifth recycle stream 135, the second vapor steam 140, the third distillation column 141, the fourth condenser 142, the fourth reboiler 144, the first product stream 112, the system recycle stream 115, the second product stream 118, the second recycle stream 136, and the third recycle stream 139. In this embodiment, a column feed stream 143 is fed into a fourth distillation column 149. The column feed stream 143 is separated into a third product stream 146 a third mixture stream 151 and a fourth mixture stream 154. The third mixture stream 151 is fed into the second distillation column 133. The fourth mixture stream 154 is fed into a fifth distillation column 157. The fourth mixture stream 154 is separated into a fourth product stream 163 and a fourth recycle stream, 160. At least a portion of the fourth recycle stream 160 is fed back into the toluene disproportionation unit 103. In an embodiment, not shown in the figures, the portion of the fourth recycle stream 160 which is not fed back into the toluene disproportionation reactor 103 is taken as product or is fed into another system. In an embodiment the first distillation column 121 is thermally coupled to the second distillation column 133 and the third distillation column 141. When the first distillation column 121 is thermally coupled to the second distillation column 121 and the third distillation column 141 the vapor side stream 126 is fed into the first distillation column 121 from the third distillation column 141 at the same stage as the second mixture stream 127 is withdrawn. Additionally, when the first distillation column 121 is thermally coupled to the second distillation column 133 and the third distillation column 141 the liquid side stream 125 is fed into the first distillation column 121 from the second distillation column 133 at the same stage as the first mixture stream 124 is withdrawn. When this configuration is implemented the reboiler 122 and condenser 120 are not necessary on the first distillation column. In an alternative embodiment, when the first distillation column 121 is thermally coupled to the second distillation column 121 and the third distillation column 141 the vapor side stream 126 is fed into the first distillation column 121 from the third distillation column 141 at a location plus or minus five stages from the stage that the second mixture stream 127 is withdrawn. Additionally, in an alternative embodiment, when the first distillation column 121 is thermally coupled to the second distillation column 133 and the third distillation column 141 the liquid side stream 125 is fed into the first distillation column 121 from the second distillation column 133 at a location plus or minus five stages from the stage that the first mixture stream 124 is withdrawn. Independently, the second distillation column 133 and the third distillation column 141 can be thermally coupled to one another by either of the two methods described above with reference to FIG. 3. In an embodiment the system recycle stream 115 comprises the second recycle stream 136, the third recycle stream 139, the fourth recycle stream 160, and the fifth recycle stream 135.

In an embodiment the fourth distillation column 149 has between about 50 and 80 theoretical stages. The third product stream is removed from the fourth distillation column 149 at between about the top theoretical stage and the theoretical stage that is fifth from the top. The column feed stream 143 is fed into the fourth distillation column 149 at between about theoretical stage number 35 and 25. The third mixture stream 151 is removed from the fourth distillation column 149 at between about theoretical stage number 55 and 45. The fourth mixture stream 154 is removed from the fourth distillation column 149 at between about the bottom theoretical stage and the theoretical stage that is fifth from the bottom. In an embodiment the fifth distillation column 157 has between about 45 and 70 theoretical stages. The fourth mixture stream 154 is fed into the fifth distillation column 157 at between about theoretical stage number 35 and 25. The fourth recycle stream 160 is removed from the fifth distillation column 157 at between about the top theoretical stage and the theoretical stage that is fifth from the top. The fourth product stream 163 is removed from the fifth distillation column 157 at between about the bottom theoretical stage and the theoretical stage that is fifth from the bottom.

In an embodiment the ranges of concentrations of the species found in the column feed steam 143 comprises between about 10 mole percent to about 50 mole percent toluene, between about 20 mole percent to about 60 mole percent benzene, between about 0 mole percent to about 40 mole percent alkyl benzene, and between about 0 mole percent to about 10 mole percent impurities. In an embodiment, the column feed stream contains between about 30 mole percent to about 60 mole percent benzene, preferably between about 30 mole percent to about 45 mole percent benzene. In an embodiment, the column feed stream contains between about 10 mole percent to about 50 mole percent toluene, preferably between about 30 mole percent to about 45 mole percent benzene. In an embodiment, the column feed stream contains between about 0 mole percent to about 40 mole percent alkyl benzene, preferably between about 15 mole percent to about 35 mole percent alkyl benzene. In an embodiment, the column feed stream contains between about 0 mole percent to about 10 mole percent impurities, preferably between about 0 mole percent to about 5 mole percent impurities.

In an embodiment the ranges of concentrations of the species found in the fourth mixture stream 154 comprises between about 40 mole percent to about 100 mole percent toluene, between about 0 mole percent to about 20,000 mole ppm benzene, between about 0 mole percent to about 50 mole percent alkyl benzene, and between about 0 mole percent to about 10 mole percent impurities. In an embodiment, the column feed stream contains between about 0 mole percent to about 20,000 mole ppm benzene, preferably between about 0 mole percent to about 500 mole ppm benzene. In an embodiment, the column feed stream contains between about 40 mole percent to about 100 mole percent toluene, preferably between about 40 mole percent to about 60 mole percent toluene. In an embodiment, the column feed stream contains between about 0 mole percent to about 50 mole percent alkyl benzene, preferably between about 30 mole percent to about 50 mole percent alkyl benzene. In an embodiment, the column feed stream contains between about 0 mole percent to about 10 mole percent impurities, preferably between about 0 mole percent to about 5 mole percent impurities.

In an alternative embodiment the system shown in FIG. 4 operates without the reactor feed stream 100 and relies solely on the column feed stream 143 as a feed source of toluene. In an embodiment the ranges of concentrations of the species found in the third product stream 151 are same as the ranges of concentrations of the species found in first product stream 124. In an embodiment the ranges of concentrations of the species found in the fourth product stream 163 are same as the ranges of concentrations found in the second product stream 118. In an embodiment the ranges of concentrations of the species found in the fourth recycle stream 160 are same as the ranges of concentrations found in the system recycle stream 115.

Figure 5:
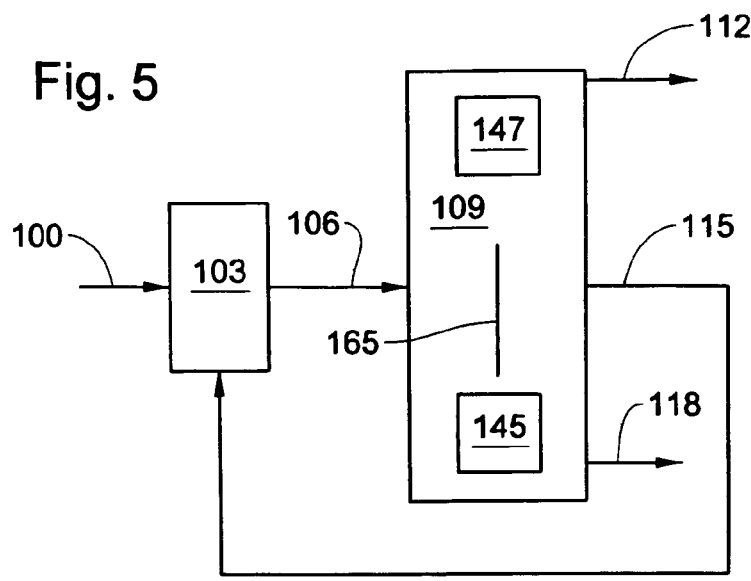
FIG. 5 is a schematic diagram of an embodiment showing a toluene disproportionation unit 103, and a divided wall column 109.

With reference to FIG. 5, in an embodiment the stream 106 is fed into a divided wall column 109. FIG. 5 shows the reactor feed stream 100, the toluene disproportionation unit 103, the feed stream 106, the first product stream 112, the system recycle stream 115, and the second product stream 118, which were described in FIGS. 1 and 2. The divided wall column has a seventh condenser 147 and a seventh reboiler 145. The divided wall column 109 comprises a divided wall 165, which is a vertical partition that segregates the fractionation zones. The placement of the divided wall 165 is a function of the position of the vertical partition along a cross section of the divided wall column 109 and the tray hydraulics. The placement of the vertical partition and the tray hydraulics should be such that the internal vapor flow up the feed side of the column is about 35% to about 50%, alternatively, 40% to about 50% of the total vapor flow, and the internal liquid flow down the product side is about 65% to about 80%, alternatively, 65 percent to about 75 percent of the total liquid flow. The term tray hydraulics is meant to embody the design of the actual trays as well as the design of the packed-beds. Suitable divided wall columns are described in U.S. Pat. No. 6,250,106 to Agrawal and U.S. Pat. No. 2,471,134 to Wright, which are both fully incorporated by reference. The divided wall column 109 preferably separates the stream 106 into a first product stream 112 a system recycle stream 115 and a second product stream 118.

In one embodiment, the total heat duty on a heating apparatus of the divided wall column 109 is from than about less than about 75,000 kJ/(kg mol product), more preferably less than about 70,000 kJ/(kg mol product), more preferably less than about 65,000 kJ/(kg mol product), most preferably less than about 63,000 kJ/(kg mol product). In an embodiment the heating apparatus of the divided wall column is the seventh reboiler 145.

Figure 6:
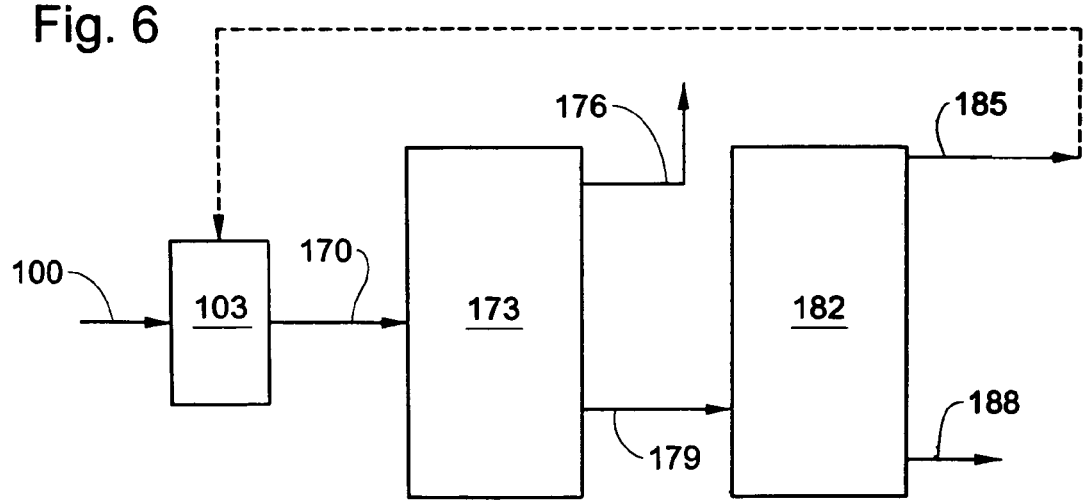
FIG. 6 is a schematic diagram of an embodiment showing the operation of a distillation system having a toluene disproportionation unit in combination with a conventional fractionation system.
Figure 7:
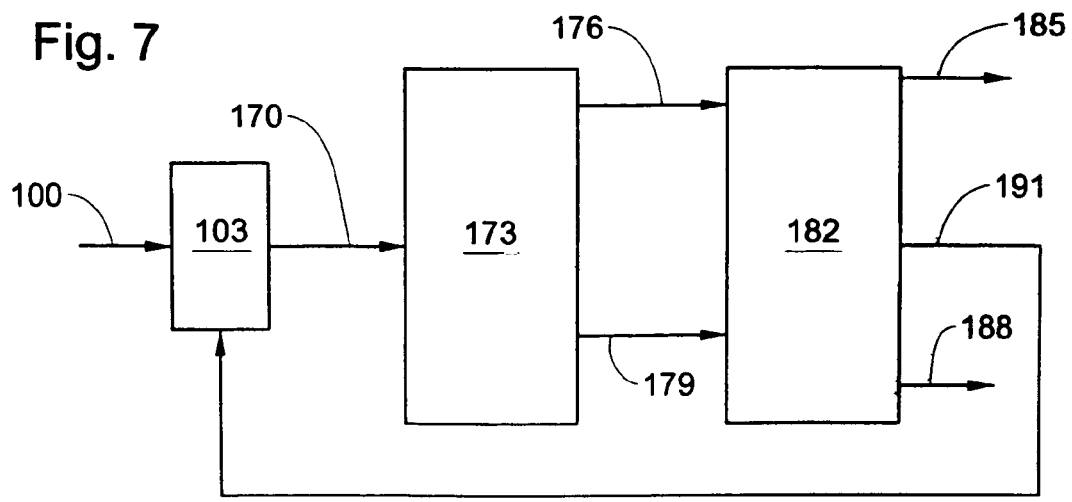
FIG. 7 is a schematic diagram of an embodiment showing the operation of a distillation system having been improved and having a toluene disproportionation unit 103, a first distillation column 173, and a second distillation column 182.

With reference to FIGS. 6 and 7, FIG. 6 shows a distillation system prior to the improvements, whereas FIG. 7 shows the distillation system post to the improvements. The reboilers and condensers have been left out of FIGS. 6 and 7 for reasons of readability. For completeness, there would be one condenser and one reboiler on each of the columns. The distillation system of FIG. 6 shows the stream 100, which is fed into the toluene disproportionation unit 103. The stream 100 and the toluene disproportionation unit 103 have been described above with reference to FIG. 1. With reference to FIG. 6, the toluene disproportionation unit 103 is fluidically connected via a feed pipe 170 to a first distillation column 173. The first distillation column 173 comprises a first overhead product pipe 176 and a bottoms mixture pipe 179. The bottoms mixture pipe 179 is fluidically connected to a second distillation column 182. In this embodiment, the said second distillation column 182 comprises a second overhead product pipe 185 and a first bottoms product pipe 189. In an alternative embodiment the second overhead product pipe 185 is fluidically connected to the toluene disproportionation unit 103, as shown by the dashed portion of the second overhead product pipe 185.

FIG. 7 shows a distillation system of the invention. The distillation system of FIG. 7 shows the stream 100, which is fed into the toluene disproportionation unit 103. The stream 100 and the toluene disproportionation unit 103 have been described above with reference to FIG. 1. With reference to FIG. 7, the improvements are made according to the following method, and the steps are presented in no particular order. The first overhead product pipe 176 is fluidically connected to the second distillation column 182. A first middle product pipe 191 is fluidically connected to the second distillation column 182. This method will require the alteration of the heat duties on the first distillation column 173 and the second distillation column 182. It is excepted that the heat duty on the first distillation column 173 is reduced whereas the heat duty on the second distillation column 182 is increased. In an embodiment, the reduction of the heat duty on the first distillation column 173 is with reference to the heat duty on the first distillation column 173 prior to improvements. In an embodiment, the increase of the heat duty on the second distillation column 182 is with reference to the heat duty on the second distillation column 182 prior to improvements. The heat duties are changed in a manner that reduces the total heat duty by at least about 10 percent over the pre-improved distillation system, preferably at least about 15 percent over the pre-improved distillation system, more preferably at least about 20 percent over the pre-improved distillation system. In an alternative embodiment the improvement method includes the steps described above and the additional steps of detaching the second overhead product pipe 185 from the toluene disproportionation unit 103, and fluidically connecting the first middle product pipe 191 to the toluene disproportionation unit 103, as shown by the dashed portion of the first middle product pipe 191.

EXAMPLES

The Comparative Example, Example 1, and Example 2 are simulations conducted in the distillation design software Simulation Science Pro/II, by Invensys plc. The following assumptions and requirements were selected in the software: a Peng-Robinson thermodynamic method, the column overhead pressure was 156.5 kPa, the columns had a pressure drop of 1.04 kPa per theoretical stage, the change in pressure on the reboiler was equal to the change in pressure per theoretical stage, the condenser pressure on all columns was 135.8 kPa, and the condenser was assumed to run at the bubble point. The aggregate number of theoretical stages in Example 1 is the same as the aggregate number of theoretical stages in the Comparative Example. The aggregate number of theoretical stages in Example 2 is less than the aggregate number of theoretical stages in the Comparative Example. The divided wall column was simulated using two separate columns. One column represented the overall divided wall column and the other column represented the divided wall. In the simulation the pressures, temperatures, and compositions where made equal at the points where in reality the overall divided wall column and the column representing the divided wall would merge. In this manner, the simulation most accurately represents a single column. In other words, in the simulation, the interconnecting streams between the overall divided wall column and the divided wall were converged to accurately represent single column operation. Moreover, the column representing the divided wall was simulated as operating without a condenser or reboiler. Instead the vapor and liquid from the overall divided wall column was used to perform the equilibrium calculations of the column representing the divided wall.

Comparative Example Plant shows data taken from a chemical plant before improvements were made. The plant data is given in terms of actual trays as opposed to theoretical stages. Trays are numbered from the bottom to the top, which is opposite from the numbering of theoretical stages. Stream data was collected using the plant's gas chromatography analyzers and/or laboratory gas chromatography analyzers. These analyzers normally have an error of plus or minus one percent if they are measuring to an accuracy above 1 percent, plus or minus five percent if they are measuring to an accuracy from 1,000 to 10,000 ppm, plus or minus 10 percent if they are measuring to an accuracy from 10 to 1,000 ppm, and plus or minus 20 percent if they are measuring to an accuracy less than 10 ppm. The data was collected over a period of six days. The first distillation column is smaller in Comparative Example Plant than the first distillation column in Comparative Example and the product streams of Comparative Example Plant are more pure than the product streams of the other examples. In this manner one could argue that higher total heat duty shown in Comparative Example Plant was due to the extra heat duty necessary to increase the purity of the product streams. However, the simulated data shows that there is an appreciable net gain in efficiency.

Example 3 Plant shows data taken from a chemical plant after improvements were made. The plant data is given in terms of actual trays as opposed to theoretical stages. Stream data was collected using the plant's gas chromatography analyzers. These analyzers normally have an error of plus or minus one percent if they are measuring to an accuracy above 1 percent, plus or minus five percent if they are measuring to an accuracy from 1,000 to 10,000 ppm, plus or minus 10 percent if they are measuring to an accuracy from 10 to 1,000 ppm, and plus or minus 20 percent if they are measuring to an accuracy less than 10 ppm. The data was collected over a period of four days. The simulated data because the plant data includes the third mixture stream 151 as an extra feed stream. However, it should be noted that even with the third mixture stream 151 acting as an extra feed stream, Example 3 Plant shows a total heat duty less than 61,000 kJ/(kg mol product). Example 3 Plant also shows that the total heat duty per total feed was less than 57,000 kJ/(kg mol feed).

COMPARATIVE EXAMPLE

In the comparative example the fractionation distillation system was applied downstream of a toluene disproportionation unit. The comparative example can best be understood by an examination of FIG. 6. However, FIG. 6 was not drawn to specifically embody the comparative example. A fluid stream comprising three major components; benzene, toluene, and alkyl benzene, was fed into a toluene disproportionation unit. Within the toluene disproportionation unit the effluent of the toluene disproportionation reactor was modified such that the effluent contained about 15.2 mole percent benzene, 70.4 mole percent toluene, 13.8 mole percent alkyl benzene, the balance mole percent was byproducts, the temperature was 140.6° C., and the pressure was 790.8 kPa. The effluent of the toluene disproportionation unit was then fed into a first distillation column. The heat duty on the reboiler of the first distillation column was 32,958 kJ/(kg mole product). The first distillation column had 60 theoretical stages. The effluent of the toluene disproportionation unit was fed into the 23rd theoretical stage of the first distillation column. In the comparative example, a top effluent of the first distillation column was taken off of the top theoretical stage as benzene product, and contained about 99.9915 mole percent benzene, about 85 mole ppm toluene, and the balance impurities. A bottoms effluent of the first distillation column was taken off of the bottom theoretical stage and fed into a second distillation column. The second distillation column had 45 theoretical stages. The top product of the second distillation column was taken off of the top theoretical stage and was about 99.59 mole percent toluene, 1470 mole ppm benzene, 2540 mole ppm alkyl benzene, and the balance impurities. The top product of the second distillation column was fed back into the toluene disproportionation unit. The bottoms product of the second distillation column was taken off of the bottom theoretical stage and was about 93.7 mole percent alkyl benzene, about 2.3 mole percent toluene, and the balance impurities. The heat duty on the reboiler of the second distillation column was about 50,658 kJ/(kg mole product). The total reboiler heat duty of the comparative example was about 83,616 kJ/(kg mole product).

COMPARATIVE EXAMPLE PLANT

Comparative Example Plant can best be understood by an examination of FIG. 6; however, FIG. 6 was not drawn to specifically embody Comparative Example Plant. The discussion of Comparative Example Plant will make use of the numbering scheme incorporated into FIG. 6 for reasons of convenience only. For example, while in FIG. 6 numeral 170 was designated as a feed pipe in the discussion above, for the purposes of Comparative Example Plant numeral 170 is designated a feed stream.

In Comparative Example Plant the effluent of the toluene disproportionation unit 103 was a stream 170, and was fed into a first distillation column 173 at tray 30. The first distillation column 173 split the stream 170 into a first product stream 176 and a first mixture stream 179. The first distillation column 173 had 49 trays, a bottoms pressure of 217 kPa, a heat duty of 53,618 kJ/(kg mol product), an overhead pressure of 158.2 kPa, and a condenser pressure of 130.6 kPa. The first product stream 176 exited the first distillation column 173 through the condenser (not shown in FIG. 6). The first mixture stream 179 was fed from the bottom of the first distillation column 173 into the 26th tray of a second distillation column 182. The second distillation column 182 had 50 trays, an overhead pressure of 196 kPa, and a bottoms pressure of 243 kPa. The condenser (not shown in FIG. 6) on the second distillation column 182 had a pressure of 168 kPa. The second distillation column 182 separated the first mixture stream 179 into a first product stream 185 and second product stream 188. The first product stream 185 was taken off of the top of the second distillation column 182, and at least a portion of the first product stream 185 was fed back into the toluene disproportionation unit 103. The second product stream 188 was taken off of the bottom of the second distillation column 182.

The stream 170 contained 15.47 mol percent benzene, 70.66 mole percent toluene, 12.62 mole percent alkyl benzene, and 1.25 mole percent byproducts. The first product stream 176 contained 96.33 mole percent benzene, and 3.67 mole percent toluene. The first product stream 185 contained 99.90 mole ppm toluene, 3 mole ppm benzene, 5,280 mole ppm alkyl benzene, and 0.52 mole percent impurities. The second product stream 188 contained 94.86 mole percent alkyl benzene, 0.55 mole percent toluene, and 4.59 mole percent impurities.

The total heat duty on Comparative Example Plant was 100,400 kJ/(kg mol product).

Example 1

In the first example the fractionation distillation system was applied downstream of a toluene disproportionation unit. The first example can best be understood by an examination of FIGS. 2 and/or 7. However, FIGS. 2 and 7 were not drawn to specifically embody the first example. In the first example, a fluid stream comprising three major components; benzene, toluene, and alkyl benzene, was fed into a toluene disproportionation unit. Within the toluene disproportionation unit the effluent of the toluene disproportionation reactor was modified such that the effluent contained about 15.2 mole percent benzene, 70.4 mole percent toluene, 13.8 mole percent alkyl benzene, the balance mole percent was byproducts, the temperature was 140.6° C., and the pressure was 790.8 kPa. The effluent of the toluene disproportionation unit was then fed into a first distillation column. The heat duty on the reboiler of the first distillation column was about 27,823 kJ/(kg mole product). The first distillation column had 38 theoretical stages. The effluent of the toluene disproportionation was fed into theoretical stage number 17 of the first distillation column. The effluent from the first distillation column was taken off of the top theoretical stage and fed into theoretical stage number 15 of a second distillation column. The second distillation column had 67 theoretical stages. The top product of the second distillation column was taken off of the top theoretical stage of the second distillation column and was about 99.9915 mole percent benzene, 85 mole ppm toluene, and the balance impurities. The bottoms product of the second distillation column was taken off of the bottom theoretical stage of the second distillation column and was about 93.7 mole percent alkyl benzene, about 2.3 mole percent toluene, and the balance was impurities. The recycle line of the second distillation column was taken off of theoretical stage number 43 of the second distillation column and was about 99.59 mole percent toluene, about 1626 mole ppm benzene, about 2540 mole ppm alkyl benzene, and the balance impurities. The recycle line of the second distillation column was fed back into the toluene disproportionation unit. The heat duty on the reboiler of the second distillation column was about 37,868 kJ/(kg mole product). The total reboiler heat duty of the first example was about 65,691 kJ/(kg mole product).

As can be seen by comparing the total reboiler heat duty of the comparative example with the total reboiler heat duty of the first example, at least a 20% reduction in overall energy was achieved. The simulations were based assuming that 1) the number of overall theoretical stages was held constant to maintain comparable capitol investment costs; 2) the number of stages in each column was optimized to minimize energy input; 3) equal feed and product compositions were used; 4) the columns operated at a constant overhead pressure; 5) the products from the columns were liquid products, specifically, the overhead product of the first distillation column in both the comparative case and example 1 was a liquid at its bubble point; 6) the stage pressure drop was held constant; and 7) the feed point locations were optimized.

Example 2

The second example can best be understood by an examination of FIG. 5. However, FIG. 5 was not drawn to specifically embody the second example. In the second example the fractionation distillation system, a divided wall column, was applied downstream of a toluene disproportionation unit. In this example the vertical partition was placed along a cross section of the divided wall column such that the internal vapor flow into the feed side of the divided wall was 42.8% of the total vapor flow and the internal liquid flow into the feed side of the divided wall was 28.3% of the total liquid flow. A fluid stream comprising three major components; benzene, toluene, and alkyl benzene, was fed into a toluene disproportionation unit. Within the toluene disproportionation unit the effluent of the toluene disproportionation reactor was modified such that the effluent contained about 15.2 mole percent benzene, 70.4 mole percent toluene, 13.8 mole percent alkyl benzene, the balance mole percent was byproducts, the temperature was 140.6° C., and the pressure was 790.8 kPa. The condenser pressure was 135.8 kPa, the column overhead pressure was 156.48 kPa, and the column bottoms pressure was 230.95 kPa. The effluent of the toluene disproportionation unit was then fed into a divided wall column. The divided wall column had a total of 74 theoretical stages. The divided wall contained 36 stages and was placed into the divided wall column between the theoretical stage that was 16th from the top and the theoretical stage that was 22nd from the bottom. The fluid stream was fed into the divided wall column at about theoretical stage number 43. The benzene product stream was removed from the top theoretical stage of the divided wall column. The benzene product stream contained about 99.99 mole percent benzene, about 85 mole ppm toluene, about less than one mole ppm alkyl benzene, and the balance impurities. The toluene product stream was removed from about theoretical stage number 24. The toluene product stream contained about 1633 mole ppm benzene, about 99.59 mole percent toluene, about 2444 mole ppm alkyl benzene, and the balance impurities. The alkyl benzene product stream was removed from the bottom theoretical stage of the divided wall column. The alkyl benzene product stream contained about less than one mole ppm benzene, about 2.31 mole percent toluene, about 93.66 mole percent alkyl benzene, and the balance impurities. The heat duty on the reboiler of the divided wall column was about 62,955 kJ/(kg mol product).

As can be seen by comparing the total reboiler heat duty of the comparative example with the total reboiler heat duty of the second example, at least a 24% reduction in overall energy was achieved.

Example 3 Plant

Example 3 Plant can best be understood by an examination of FIG. 4, specifically the boxed portion 170; however, FIG. 4 was not drawn to embody Example 3 Plant. The discussion of Example 3 Plant will make use of the numbering scheme incorporated into FIG. 4 for reasons of convenience only. Example 3 Plant deviates from the boxed portion 170 in that in Example 3 Plant there is a heat exchanger connected to the first mixture stream 124.

In Example 3 Plant the effluent of the toluene disproportionation unit 103 was the stream 106, and was fed into the first distillation column 121 at tray 20. The first distillation column 121 split the stream 106 into a first mixture stream 124 and a second mixture stream 127. The first distillation column 121 had 49 trays, a bottoms pressure of 242.7 kPa, a heat duty on the reboiler 122 of 29,357 kJ/(kg mole product), a reflux temperature of 63.8° C., an overhead pressure of 184.1 kPa, and a condenser pressure of 156.5 kPa on the condenser 120. The first mixture stream 124 exited the first distillation column 121 through the condenser 120 and into a heat exchanger (not shown in FIG. 4). The heat exchanger had a duty of about 5,659 kJ/(kg mole product) and heated the first mixture stream 124 to a temperature of 132° C. and a pressure of 400 kPa. The first mixture stream 124 was fed into the second distillation column 133 at the 25th tray. The second mixture stream 127 was fed from the bottom of the first distillation column 121 into the 20th tray of the third distillation column 141. The second distillation column 133 had 50 trays and an overhead pressure of 189.6 kPa. The third condenser 129 on the second distillation column 133 had a pressure of 165.5 kPa. The third distillation column 141 had 49 trays, a bottom pressure of 295.8 kPa, and a heat duty on the fourth reboiler 144 of 31,008 kJ/(kg mole product). The second distillation column 133 and the third distillation column 141 were thermally coupled to each other through a second liquid stream 134 and a second vapor stream 140. The second distillation column 133 separated the first mixture stream 124 into a first product stream 112 and a system recycle stream 135. The system recycle stream 135 was taken off of the second liquid stream 134 and fed back into the toluene disproportionation unit 103. The third distillation column separated the second mixture stream 127 into a second vapor stream 140 and a second product stream 118.

The stream 106 had a temperature of 138.9° C., a pressure of 790 kPa, 16.58 mol percent benzene, 70.64 mole percent toluene, 12.22 mole percent alkyl benzene, 0.56 mole percent byproducts. The first mixture stream 124 was 33.72 mole percent benzene, 65.85 mole percent toluene, 1483 mole ppm alkyl benzene, and 0.27 mole percent impurities. The second mixture stream 127 was 319 mole ppm benzene, 72.09 mole percent toluene, 23.13 mole percent alkyl benzene, and 4.74 mole percent impurities. The first product stream 112 was 82 mole ppm toluene and the balance benzene. The second product stream 118 was 95.75 mole percent alkyl benzene, 1.71 mole percent toluene, and 2.53 percent impurities. The system recycle stream 115 was 2845 mole ppm alkyl benzene, 370 mole ppm benzene, and 99.68 mole percent toluene. The third mixture stream 151 had a temperature of 115.8° C., a pressure of 200 kPa, 38.0 mole percent benzene, and 62.0 mole percent toluene. The third mixture stream 151 was fed into the second distillation column 133 at a molar feed rate of 7.64 percent of the stream 106.

The total heat duty on Example 3 Plant was 60,348 kJ/(kg mol product) or 56,065 kJ/(kg mol feed). The total heat duty does not take into account the heat duty of the heat exchanger above the first distillation column 121.

All documents described herein are incorporated by reference herein, including any priority documents and/or testing procedures. As is apparent from the foregoing general description and preferred embodiments, while forms of the invention have been illustrated and described, various modifications can be made without departing from the spirit and scope of the invention. Accordingly, it is not intended that the invention be limited to the specific embodiments described in this application.

I claim:

1. A method for separating a stream having benzene, toluene and alkyl benzene, said method comprising:
   a. feeding the stream into a first distillation column, wherein the stream comprises between about 60 mole percent to about 85 mole percent toluene, between about seven mole percent to about 20 mole percent benzene, and between about seven mole percent to about 20 mole percent alkyl benzene,
   b. separating the steam into a first mixture stream and a second mixture stream,
   c. feeding the first mixture stream and the second mixture stream into a distillation system, and
   d. separating the first mixture stream and the second mixture stream into a first product stream, a system recycle stream, and a second product stream.

2. The method of claim 1, wherein at least a portion of the system recycle stream is fed into a toluene disproportionation unit.

3. The method of claim 2, wherein the stream is the effluent disproportionated from a toluene disproportionation unit.

4. The method of claims 1 or 3, wherein the first distillation column is thermally coupled to the distillation system.

5. The method of claim 1, wherein said distillation system comprises a second distillation column and a third distillation column, and wherein the method is further comprising:
   a feeding the first mixture stream into the second distillation column,
   b. separating the first mixture stream into the first product stream and a second recycle stream,
   c. feeding the second mixture stream into the third distillation column,
   d. separating the second mixture stream into the second product stream and a third recycle stream, wherein the system recycle stream comprises the second recycle stream and the third recycle stream.

6. The method of claim 5 wherein the second distillation column is thermally coupled to the third distillation column.

7. The method of claims 5 or 6, wherein at least a portion of the system recycle stream is fed into a toluene disproportionation unit.

8. The method of claim 5, 6 or 7, wherein the distillation system includes a fourth distillation column and a fifth distillation column, said method comprising:
   a. feeding a column feed stream into the fourth distillation colunm, wherein the column feed stream comprises between about 10 mole percent to about 50 mole percent toluene, between about 20 mole percent to about 60 mole percent benzene, between about 0 mole percent to about 40 mole percent alkyl benzene, and between about 0 mole percent to about 10 mole percent impunties,
   b. separating the column feed stream into a third product stream, a third mixture stream, and a fourth mixture stream,
   c. feeding the third mixture stream into the second distillation column,
   d. feeding the fourth mixture stream into the fifth distillation column, e. separating the fourth mixture stream into a fourth recycle stream and a fourth product stream, and f. feeding at least a portion of the fourth recycle steam into the toluerie disproportionation unit.

9. A method for separating a stream having benzene, toluene and alkyl benzene, said method comprising:

a. feeding the stream into a divided wall column, wherein the stream comprises between about 60 mole percent to about 85 mole percent toluene. between about seven mole percent to about 20 mote percent beazene, and between about seven mole percent to about 20 mole percent alkyl benzene, and b. separating the stream into a first product stream, a system recycle stream, and a second product stream.

10. The method of claim 9, wherein at least a portion of the system recycle stream is fed into a toluene disproportionation unit.

11. The method of claim 10, wherein the stream is the effluent produced from feeding a reactor feed stream into the toluene disproportionation unit.

12. An apparatus comprising a toluene disproportionation unit, a first distillation column and a distillation system, wherein a stream having between about 60 mole percent to about 85 mole percent toluene, between about seven mole percent to about 20 mole percent benzene, and between about seven mole percent to about 20 mole percent alkyl benzene is fed into the first distillation column, and wherein a first mixture stream is fed from the first distillation column into the distillation system, and a second mixture stream is fed from the first distillation column into the distillation system, and at least a portion of the system recycle stream is fed from the distillation system into the toluene disproportionation unit, wherein the distillation system comprises a second distillation column, a third distillation column, wherein the first mixture stream is fed from the first distillation column into the second distillation column, the second mixture stream is fed from the first distillation column into the third distillation column, and at least a portion of the second recycle stream from the second distillation column and/or the third recycle stream from the third distillation column is/are fed into the toluene disproportionation unit.

13. The apparatus of claim 12, wherein the stream is the effluent disproportionated from the toluene disproportionation unit.

14. The apparatus of claim 12 or 13, wherein a column feed stream having between about 10 mole percent to about 50 mole percent toluene, between about 20 mole percent 10 about 60 mole percent benzene, between about 0 mole percent to about 40 mole percent alkyl benzene, and between about 0 mole percent to about 10 mole percent impurities is fed into a fourth distillation column, a third mixture stream is fed into the second distillation column from the Fourth distillation column, a fourth mixture stream is fed from the fourth distillation column into a fifth distillation column, and at least a portion of a fourth recycle stream is fed from the fifth distillation column into the toluene disproportionation unit.

15. The apparatus of claim 14, wherein the second distillation column is thermally coupled to the third distillation column.

16. The apparatus of claim 12, wherein said first distillation column comprising a divided wall column.

17. A method for improving the operation of a distillation system, said distillation system having a toluene disproportionation unit fluidically connected to a first distillation column, wherein said first distillation column comprises a first overhead product pipe and a bottoms mixture pipe, wherein said bottoms mixture pipe is fluidically connected to a second distillation colunm, wherein said second distillation column comprises a second overhead product pipe and a first bottoms product pipe, said method including the steps of:

a. reducing the heat duty on the first distillation column;

b. fluidically connecting the first overhead product pipe to the second distillation column;

c. increasing the heat duty on the second distillation column; and d. providing a first middle product pipe fluidically connected to the second distillation column; wherein the heat duty on the first distillation column and the heat duty on the second distillation column are changed in a manner that reduces the total heat duty by at least about 15 percent.

18. The method for improving the operation of a distillation system of claim 17, wherein the second overhead product pipe of the distillation system is fluidically connected to the toluene disproportionation unit, said method including the steps of:

a. detaching the second overhead product pipe from the toluene disproportionation unit, and b. fluidically connecting the first middle product pipe to the toluene disproportionation unit.

19. The apparatus of claim 12, wherein the second distillation column is thermally coupled to the third distillation column.

20. The apparatus of claim 13, wherein the second distillation column is thermally coupled to the third distillation column.

* * * * *